US008273877B1

(12) United States Patent
Stern et al.

(10) Patent No.: US 8,273,877 B1
(45) Date of Patent: Sep. 25, 2012

(54) SUBSTITUTED TETRAAZAPENTALENES

(75) Inventors: Alfred G. Stern, Upper Marlboro, MD (US); Patrick A. Caruana, Waldorf, MD (US)

(73) Assignee: The United States of America as Represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 13/373,540

(22) Filed: Nov. 18, 2011

(51) Int. Cl.
*C07D 473/16* (2006.01)
*C07D 249/06* (2006.01)
*C09B 29/52* (2006.01)
*C09B 41/00* (2006.01)
*C06B 25/34* (2006.01)

(52) U.S. Cl. ........ 544/247; 544/254; 548/255; 548/256; 548/257; 548/258; 548/259; 548/260; 548/261; 534/581; 534/590; 149/105; 149/122

(58) Field of Classification Search .................. None
See application file for complete search history.

(56) References Cited

U.S. PATENT DOCUMENTS

| 2,543,333 | A | * | 2/1951 | Parker et al. .................. 544/254 |
| 3,131,102 | A | | 4/1964 | Kenney |
| 3,166,567 | A | | 1/1965 | Carboni |
| 4,157,443 | A | * | 6/1979 | Fletcher .................. 544/254 |
| 4,167,633 | A | | 9/1979 | Morrow |
| 4,340,430 | A | | 7/1982 | Roueche |
| 7,534,555 | B2 | | 5/2009 | Bedell et al. |
| 7,884,209 | B2 | | 2/2011 | Gruessing et al. |

FOREIGN PATENT DOCUMENTS

CN 102153580 * 8/2011

OTHER PUBLICATIONS

Timmis, G.M. et al., Structure-Activity Relations in Two New Series of Antifolic Acids, Journal of Pharmacy and Pharmacology, 9, 46-67, 1957.*
Ichikawa, Musubu et al., Journal of Materials Chemistry, 21(32), 11791-11799, published on the web Jul. 4, 2011.*
Shealy, Y. Fulmer et al., "Carbocyclic Analogs of Guanosine and 8-Azaguanosine", Journal of Pharmaceutical Sciences, 62(9), 1432-1434, 1973.*
Dyall, Leonard K. et al., "Oxidative Cyclizations. VIII. Mechanisms of Oxidation of ortho-Substituted Benzeneamines and Improved Cyclizations by Bis(acetato-O)phenyliodine", Australian Journal of Chemistry, 45, 371-384, 1992.*
Machine Translation of CN 102153580, Aug. 17, 2011.*

* cited by examiner

*Primary Examiner* — Fiona T Powers
(74) *Attorney, Agent, or Firm* — Fredric J. Zimmerman

(57) ABSTRACT

Substituted tetraazapentalenes have two benzenoid rings and eight substitutable positions. Substitutions are made of hydrogen or C—H groups in favor of amino groups, nitro groups or nitrogen atoms. The tetraazapentalenes are synthesized through an intermediate azo, which is made from a 1:1:1 molar ratio of a nitroaniline, sodium nitrite and an amine.

8 Claims, No Drawings

SUBSTITUTED TETRAAZAPENTALENES

STATEMENT OF GOVERNMENT INTEREST

The invention described herein may be manufactured and used by or for the Government of the United States of America for Governmental purposes without the payment of any royalties thereon or therefore.

BACKGROUND OF INVENTION

1) Field of the Invention

The present invention is directed to tetraazapentalenes and methods of making tetraazapentalenes.

2) Description of Prior Art

One type of tetraazapentalene, dibenzotetraazapentalene, has a chemical structure of the form (Drawing 1):

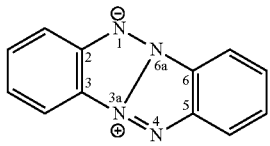

Additionally, there are isomeric forms of dibenzotetraazapentalenes. One isomeric form has the following structure (Drawing 2):

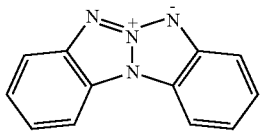

There are also other tetraazapentalene structures that contain only one benzene ring or no benzene rings.

Many tetraazapentalenes have two benzenoid rings. These benzenoid rings, which are located on the far left and far right of the illustrated chemical structure, can be substituted or unsubstituted. Each benzenoid ring has six carbon atoms; and there are four replaceable hydrogens associated with the carbon atoms on each benzenoid ring. With two rings, there are a total of eight positions in the tetraazapentalene structure that can be substituted. In addition, the carbon atoms themselves in each benzenoid ring can be substituted. The types and locations of these substitutions determine the characteristics of the resultant tetraazapentalene. Two known species of tetraazapentalene are tetranitro dibenzo tetraazapentalene ("TACOT") and tetranitro bipyrimidine tetraazapentalene ("TNBP").

TACOT is a tetranitro tetraazapentalene where four of the replaceable hydrogens are substituted with nitro groups ($NO_2$), and the four remaining replaceable hydrogens are unsubstituted. This results in the following structure (Drawing 3):

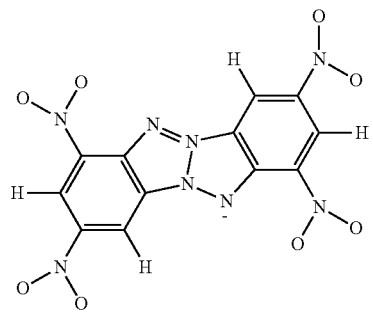

TNBP, is a tetranitro tetraazapentalene wherein the four remaining replaceable hydrogen groups in TACOT and the carbons atoms associated with those hydrogen groups are substituted with nitrogen atoms. TNBP has the following structure (Drawing 4):

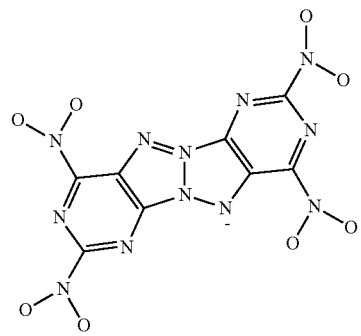

U.S. Pat. No. 3,166,567 ("the '567 patent") is directed to dibenzotetraazapentalenes, which are organic nitrogen containing cyclic compounds. Of particular note is the tetraazapentalene known as tetranitro dibenzo tetraazapentalene, which is a type of TACOT. The '567 patent lists the potential substituents nitro, halo, azido, amino and sulfonyl. For example, tetranitro dibenzo tetraazapentalenes, dichloro dibenzo tetraazapentalenes, diamino dibenzo tetraazapentalenes and diazidodinitro dibenzo tetraazapentalenes are discussed.

In Technical Report No. 47 by the Office of Naval Research and titled "Luminescent Nitro Derivatives of 5,11-Dehydro-5H,11H-benzotriazolo[2,1-a]benzotriazole", tetraazapentalenes are disclosed that have the following structure (Drawing 5):

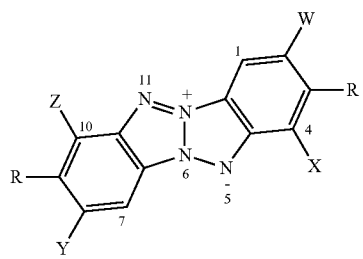

A variety of potential substituents for the Z, Y, W and X positions are provided. These substituents include nitro, amino and methyl groups. When Z=Y=W=X=$NO_2$, a tetranitro tetraazapentalene is formed.

U.S. Pat. No. 4,340,430 ("the '430 patent") is directed to a process for the production of azo, which is an intermediate found in the production of tetraazapentalene. According to the '430 patent, an amine, which could be nitroaniline, is coupled with 2,4,6-triaminopyrimidine. Sodium nitrite in an aqueous-mineral acid medium is used for diazotization of aminobenzenesulfonic or aminobenzenecarboxylic acid. In the disclosed method, 48 parts of 2-nitroaniline-4-sulfonic acid are dissolved in 750 parts by volume of water with 50 parts 30% sodium hydroxide. After filtration with 1 part of decolourising carbon, 110 parts of 30% hydrochloric acid are rapidly stirred into the clear solution. The suspension thereby obtained is cooled to 0° C., and 50 parts by volume of 4N sodium nitrite solution is introduced at 0° to 5° C. over the course of 15 minutes. The diazotization is complete after 15 minutes.

Excess nitrous acid is destroyed with urea or sulfamic acid, and the diazo suspension is adjusted to a pH of 4 to 4.5 with sodium acetate. A solution of 25 parts 2,4,6-triaminopyrimidine-1,3 in 600 parts by volume of water is added to the diazo suspension over the course of 1 hour. The temperature of the reaction mixture rises to 15° to 20° C. Stirring is continued until the coupling is complete, and the coupling mixture is then warmed to 40° to 45° C. over the course of 1 hour. The coupling mixture is then filtered. The filter cake is washed with water until it is as salt-free as possible.

Suspended in 260 parts by volume of water is 44 parts of the filter residue (16.5% aqueous paste corresponding to 7.2 parts of dry azo dyestuff sulfonic acid). After heating to 70° to 75° C., the suspension is adjusted to a pH of about 10 using 25% $NH_4OH$. A solution of 2 parts of magnesium chloride hexahydrate in 30 parts of water is added. After stirring for 10 hours at 90° to 95° C., the pigment suspension is filtered hot, and the filter cake is washed with hot water until no more chlorine ions can be detected in the filtrate. The filter cake is then dried in vacuo at 100° C.

Although TACOT has been widely used as an explosive, explosives that can produce equivalent or increased explosions in a given amount of material are desired. For example, tetraazapentalenes having increased explosive capability and greater energy per unit of material are desired. These tetraazapentalenes would also exhibit greater stability at high temperatures.

SUMMARY OF THE INVENTION

Exemplary embodiments in accordance with the present invention are directed to formulations of tetranitro dibenzotetraazapentalenes and methods for making these formulations. Many dibenzotetraazapentalenes are compounds having the following structure (Drawing 6):

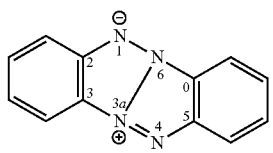

This structure includes two benzenoid rings, which are located on the far left and far right in the illustrated formula. These benzenoid rings can be substituted or unsubstituted. Each benzenoid ring has six carbon atoms: In an unsubstituted tetraazapentalene, each carbon atom is bonded to a hydrogen atom. Four of these hydrogens on each benzenoid ring are replaceable. With two benzenoid rings, this provides for a total of eight positions where substitution of hydrogens is possible. It is also possible to substitute the carbons in the benzenoid rings. For example, one or more carbon and hydrogen groups in the ring are replaced with nitrogen.

Suitable substituents for use in a substituted benzenoid ring include, but are not limited to, nitro, halo, azido, amino and sulfonyl groups. In exemplary embodiments of the present invention, nitro and amino groups are used. A nitro group has one nitrogen atom and two oxygen atoms. An amino group has one nitrogen atom and two hydrogen atoms.

In one exemplary embodiment, the groups are substituted to yield a diamino tetraazapentalene ("TAP1"). TAP1 has the chemical formula $C_{10}H_8N_8$. As illustrated in the following formula (Drawing 7), positions 1-4 in one benzenoid ring are unsubstituted, and two amino groups are substituted in positions 7 and 9 of the other benzenoid ring. Drawing 7:

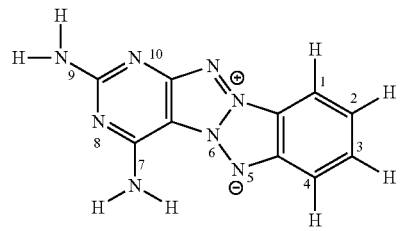

In one embodiment, the benzenoid rings are substituted to yield dinitro tetraazapentalene ("DNTAP1"). DNTAP1 has the chemical formula $C_{10}H_6N_{10}O_4$. As illustrated in the following formula (Drawing 8), DNTAP1 includes two amino groups in positions 7 and 9 of one benzenoid ring and two nitro groups at positions 2 and 4 of the other benzenoid ring. Drawing 8:

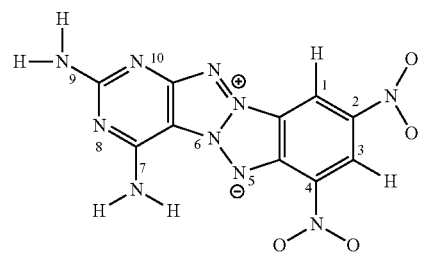

In one exemplary embodiment, the benzenoid rings are substituted to yield a tetranitro monopyrimidine tetraazapentalene ("TNMP1"). As illustrated in the following formula (Drawing 9), TNMP1 includes two nitro groups in positions 7 and 9 of one benzenoid ring and two nitro groups at positions 2 and 4 of the other benzenoid ring.

Drawing 9:

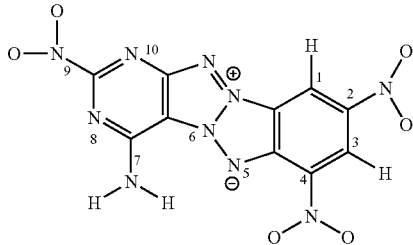

In one exemplary embodiment, the benzenoid rings are substituted to yield diamino tetraazapentalene ("TAP2"). These substitutions replace both the hydrogens and the carbons in the benzenoid rings. TAP2 is an isomer of TAP1 and has the chemical formula $C_{10}H_8N_8$. As illustrated in the following formula (Drawing 10), one of the benzenoid rings in TAP2 is unsubstituted, and the other benzenoid ring includes amino groups at locations 7 and 9 and nitrogen at locations 8 and 10. Drawing 10:

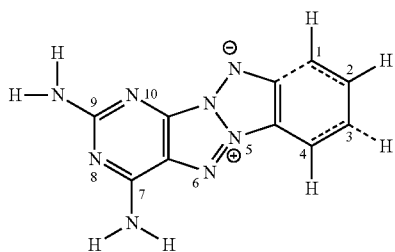

In one exemplary embodiment, the benzenoid rings are substituted to yield dinitro tetraazapentalene ("DNTAP2"), which is an isomer of DNTAP1 where carbons have been substituted with nitrogen in one of the benzenoid rings. DNTAP2 has the chemical formula $C_{10}H_6N_{10}O_4$. As illustrated in the following formula (Drawing 11), DNTAP2 includes nitro groups at locations 1 and 3 of one benzenoid ring, amino groups at locations 7 and 9 of the other benzenoid ring with nitrogens at locations 8 and 10 of those rings. Drawing 11:

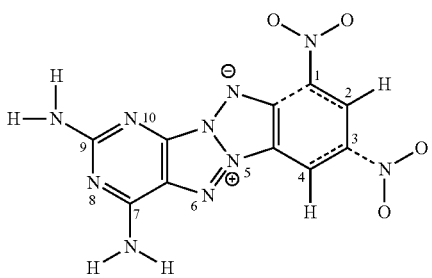

In one exemplary embodiment, the benzenoid rings are substituted to yield tetranitro monopyrimidine tetraazapentalene ("TNMP2"), which is an isomer of TNMP1 where nitrogens have been switched with carbon-nitro groups in one of the benzenoid rings. TNMP2 has the chemical formula $C_{10}H_2N_{10}O_8$. As illustrated in the following formula (Drawing 12), TNMP2 includes nitro groups at locations 1 and 3 of one benzenoid ring as well as nitro groups at locations 7 and 9 of the other benzenoid ring, which also has nitrogen at locations 8 and 10.

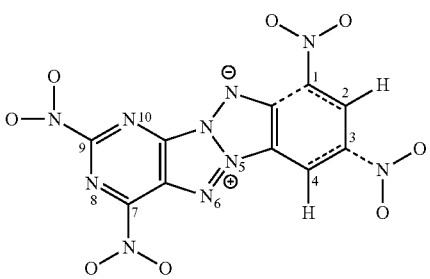

Exemplary embodiments of methods and systems in accordance with the present invention are also directed to methods for synthesizing the intermediates used in the production of tetraazapentalene including the intermediate azo. To synthesize a yield of azo, a solution containing a 1:1:1 molar ratio of an amine, such as triaminopyrimidine or 2,4,6-triaminopyrimidine, sodium nitrite and a nitroaniline, for example ortho-nitroaniline, is combined with a chemical reagent such as hydrochloric acid. Sodium nitrite is used to diazotize the amine. This yields azo, in an exemplary yield at about a 90% yield.

To continue synthesizing the desired tetraazapentalene, iodobenzene diacetate and a solvent are then added to the azo product. This results in a triazole. An exemplary embodiment triazole is depicted below. Drawing 13:

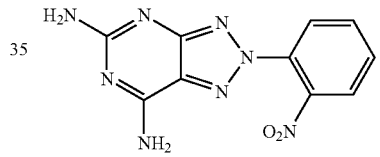

Triethylphosphite is added to the resulting triazole. The products of this reaction are TAP1 and TAP2. The next step involves nitration by treating the mixture of TAP1 and TAP2 with sulfuric acid and 99% nitric acid. This reaction yields DNTAP1, DNTAP2, and a dinitrobenzotriazole side-product.

In one exemplary embodiment, the next step includes a nitro Sandmeyer reaction. Sodium nitrite and sulfuric acid in aqueous solution are mixed with DNTAP1, resulting is a yield of TNMP1. Alternatively, sodium nitrite and acetic acid can be added to DNTAP1 to yield TNMP1. In some exemplary embodiments, an oxidizer and sulfuric acid are mixed with DNTAP1 to yield TNMP1. In other embodiments, hypofluorous acid is reacted with DNTAP1 to yield TNMP1.

Similarly TNMP2 may be obtained from DNTAP2. In one exemplary embodiment, sodium nitrite and acetic acid may be added to DNTAP2 to yield TNMP2. In some embodiments, an oxidizer and sulfuric acid are mixed with DNTAP2 to yield TNMP2. In other embodiments, hypofluorous acid is reacted with DNTAP2 to yield TNMP2.

DETAILED DESCRIPTION OF THE INVENTION

Exemplary embodiments in accordance with the present invention are directed to methods and systems that result in dibenzotetranitro tetraazapentalenes. Many dibenzotetraazapentalenes are compounds with a general structure depicted below. Drawing 14:

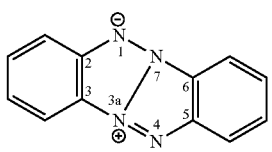

The structure includes two benzenoid rings, which are located on the far left and far right, that may be substituted or unsubstituted. Each benzenoid ring has six carbon atoms. In an unsubstituted tetraazapentalene, each carbon atom is bonded to a hydrogen atom. Four of these hydrogens on each benzenoid ring are replaceable, resulting in a total of eight positions where substitution may take place. In addition, the carbon and hydrogen pairs in each benzenoid ring can be substituted with nitrogen.

Suitable substituents for replacing the hydrogens include, but are not limited to, nitro, halo, azido, amino and sulfonyl groups. In exemplary embodiments, nitro and amino groups are used. A nitro group has one nitrogen atom and two oxygen atoms. The nitro group depicted below (Drawing 15) is bonded to a carbon atom. Drawing 15:

An amino group has one nitrogen atom and two hydrogen atoms. The amino group depicted below (Drawing 16) is bonded to a carbon atom. Drawing 16:

In one exemplary embodiment, the tetraazapentalene formed is diamino tetraazapentalene ("TAP1"). TAP1 has the chemical formula $C_{10}H_8N_8$. As illustrated in the following structure (Drawing 17), positions 1-4 in one of the benzenoid rings are unsubstituted. The hydrogen atoms of positions 7 and 9 in the other benzenoid ring have been substituted with amino groups. In addition, the carbon atoms of positions 8 and 10 of this other benzenoid ring have been substituted with nitrogen atoms. Drawing 17:

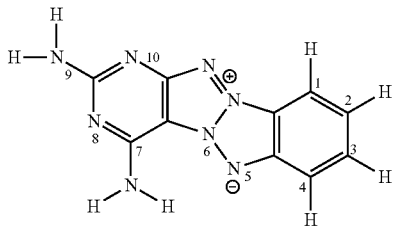

In one exemplary embodiment, the tetraazapentalene is dinitro tetraazapentalene ("DNTAP1"). DNTAP1 has the chemical formula $C_{10}H_6N_{10}O_4$. As illustrated in the following structure (Drawing 18), the hydrogen atoms of positions 2 and 4 in one of the benzenoid rings have been substituted with nitro groups. The hydrogen atoms of positions 7 and 9 of the other benzenoid ring have been substituted with amino groups. In addition, the carbon atoms of positions 8 and 10 of this other benzenoid ring have been substituted with nitrogen atoms. Drawing 18:

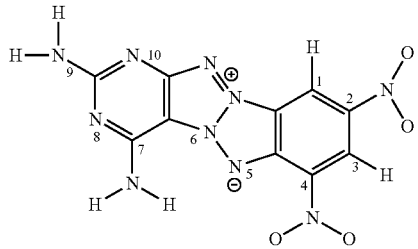

In one embodiment, the tetraazapentalene is tetranitro monopyrimidine tetraazapentalene ("TNMP1"). TNMP1 has the chemical formula $C_{10}H_2N_{10}O_8$. As illustrated in the following formula (Drawing 19), the hydrogen atoms of positions 2 and 4 of one benzenoid ring and 7 and 9 of the other benzenoid ring have been substituted with nitro groups. In addition, the carbon atoms of positions 8 and 10 of the other benzenoid ring have been substituted with nitrogen atoms. Drawing 19:

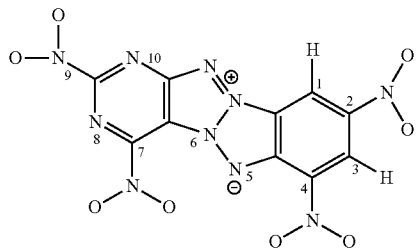

In one exemplary embodiment, the tetraazapentalene is diamino tetraazapentalene ("TAP2"), which is an isomer of TAP1 and has the chemical formula $C_{10}H_8N_8$. As illustrated in the following formula (Drawing 20), positions 1-4 of one benzenoid ring are unsubstituted. Positions 7 and 9 of the other benzenoid ring have the hydrogen atoms substituted with amino groups, and nitrogen replaces carbon at positions 8 and 10. Drawing 20:

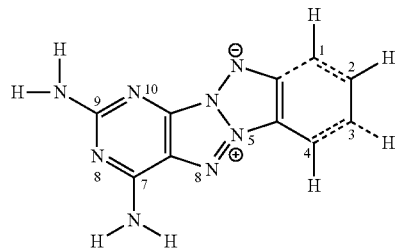

In one exemplary embodiment, the tetraazapentalene is dinitro tetraazapentalene ("DNTAP2"), which is an isomer of DNTAP1 and has the chemical formula $C_{10}H_6N_{10}O_4$. As illustrated in the following formula (Drawing 21), the hydrogen atoms in positions 1 and 3 of one of the benzenoid rings have been substituted with nitro groups. The hydrogen atoms of positions 7 and 9 of the other benzenoid ring have been substituted with amino groups, and the carbon at positions 8 and 10 of this other benzenoid ring have been substituted with nitrogen. Drawing 21:

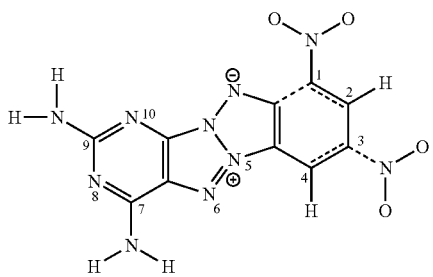

In one exemplary embodiment, tetraazapentalene is tetranitro monopyrimidine tetraazapentalene ("TNMP2"), which is an isomer of TNMP1 and has the chemical formula $C_{10}H_2N_{10}O_8$. As illustrated in the following formula (Drawing 22), the hydrogen atoms in positions 1 and 3 of one benzenoid ring have been substituted with nitro groups. The hygrogen atoms in positions 7 and 9 of the other benzenoid ring have also been substituted with nitro groups, and the carbon at positions 8 and 10 of this other benzenoid ring have been substituted with nitrogen. Drawing 22:

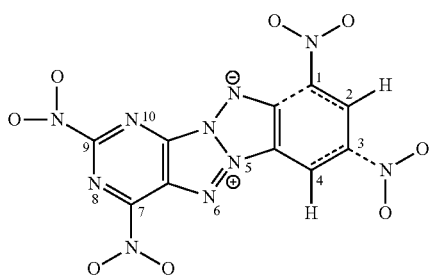

Actual Methods-Actual Results

Methods in accordance with exemplary embodiments of the present invention are directed to the production of the various embodiments of tetraazapentalenes and include the synthesis of intermediates used in the production of tetraazapentalene. These intermediates include, but are not limited to azo. In one embodiment for the synthesis of a desired yield of azo, a nitroaniline, sodium nitrite and an amine were combined in a molar ratio of about 1:1:1 with a chemical reagent. Sodium nitrite was used to diazotize the amine.

The nitroaniline, sodium nitrite and amine were reacted with the chemical reagent to produce a yield of azo. In an exemplary embodiment, the yield of azo was about 90% azo. Suitable chemical reagents include, but are not limited to, hydrochloric acid. Suitable nitroanilines include, but are not limited to, ortho-nitroaniline. Suitable amines include, but are not limited to, triaminopyrimidine, for example, 2,4,6-triaminopyrimidine.

In one exemplary embodiment, ortho-nitroaniline was first diazotized with sodium nitrite, an acid, and a solvent at a temperature of about 0° C. Suitable acids include hydrochloric (HCl) acid, and suitable solvents include dimethylformamide. The triaminopyrimidine was added to this solution, and the temperature of the reaction mixture was raised to room temperature, for example, about 20-22° C. The resulting HCl salt of azo was filtered off, washed with water, and stirred with about 10% potassium carbonate in aqueous solution at room temperature for about 20 minutes. In one embodiment, this produced about a 90% yield of azo. An exemplary azo compound is depicted below. Drawing 23:

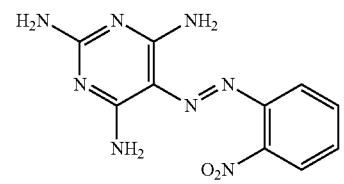

In some exemplary embodiments, 65 mL of concentrated hydrochloric acid was added to a solution of 5.0 g, 0.036 mol ortho-nitroaniline in 75 mL dimethyl formamide dropwise. The solution was stirred for 10 minutes at 3° C. 2.5 g, 0.036 mol of sodium nitrite in 18 mL of water was added dropwise to the solution. The resulting clear yellow solution was stirred for 30 minutes at 3° C. 4.53 g, 0.036 mol of 2,4,6-triaminopyrimidine was added in portions over 5 minutes. Orange/red precipitate forms with each addition of pyrimidine. 100 mL of water was added. The resulting orange/yellow heterogeneous mixture was gradually warmed to room temperature for approximately 20 hours with vigorous stirring. Filtration of the resulting orange slurry gave an HCl salt of azo, which was washed with ice-chilled water. The resulting pasty material was stirred vigorously with 450 mL of 10% potassium carbonate for 30 minutes at room temperature. The resulting red precipitate was filtered, washed with water, and air dried over several days or dried in a vacuum oven at 70° C. and 25 mmHg to give a yield of 8.86 g (90%) azo. The material was characterized as follows: mp 274° C. (broad dec); $^1$H NMR (300 MHz, DMSO-d$_6$) δ 9.54 (s, 1H), 8.23 (dd, J=8.4, 0.9 Hz, 1H), 7.89-7.80 (m, 2H), 7.62 (td, J=8.4, 1.2 Hz, 1H), 7.34 (m, 2H), 7.01 (s, 1H), 6.74 (s, 2H); $^{13}$C NMR (75 MHz, DMSO-d$_6$) δ 165.0, 164.5, 155.8, 145.9, 145.5, 133.7, 126.8, 124.7, 118.4, 113.0; IR: 3505, 3392, 3096, 1666, 1619, 1569, 1510, 1435, 1351, 1257, 1215 cm$^{-1}$; MS-DART ionization-positive (m/z): calculated for $C_{10}H_{11}N_8O_2$ [M+H]$^+$, 275.1005; found, 275.0970. Anal. Calcd. for $C_{10}H_{10}N_8O_2$: C, 43.80; H, 3.68; N, 40.86; Found: C, 42.68; H, 3.58; N, 39.20. Drawing 24:

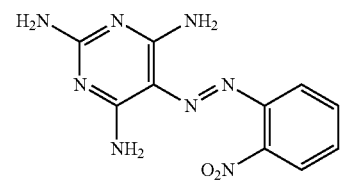

To continue with the production of tetraazapentalene, iodobenzene diacetate and a solvent were added to the azo product. Suitable solvents include, but are not limited to, dimethylformamide. The reaction occurred at room temperature for about 40 hours. This resulted in a triazole as illustrated in this structure. Drawing 25:

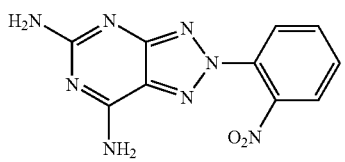

In some exemplary embodiments, 1.00 g, 0.00365 mol of azo was stirred vigorously with 80 mL of dimethyl formamide at room temperature until a homogenous red solution was obtained. In some exemplary embodiments this process took approximately 20 to 30 minutes. To the resulting solution 1.65 g, 0.00511 mol of iodobenzene diacetate was added in one portion. The resulting mixture was stirred for 40 hours at room temperature under argon. The mixture was concentrated in vacuo to give a yellow solid. The yellow solid was then rinsed with hexanes, stirred with ice-cold water for 2 minutes, filtered off, and washed with ice-cold water. The resulting solution was then dried under heat and high vacuum resulting in a yield of 0.83 g (84%) triazole as a yellow solid. The material was characterized as follows: mp 258-260° C.; $^1$H NMR (300 MHz, DMSO-$d_6$) δ 8.13 (d, J=7.8 Hz, 1H), 8.05-7.60 (m, 5H), 6.4.0 (s, 2H); $^{13}$C NMR (75 MHz, DMSO-$d_6$) δ 162.9, 160.8, 156.4, 143.4, 133.8, 131.9, 130.3, 126.1, 125.2, 125.1; IR: 3506, 3395, 3086, 1678, 1616, 1581, 1534, 1489, 1454, 1387, 1358 cm$^{-1}$; MS-DART ionization-positive (m/z): calculated for $C_{10}H_9N_8O_2$ [M+H]$^+$, 273.0849; found, 273.0848. Anal. Calcd. for $C_{10}H_8N_8O_2$: C, 44.12; H, 2.96; N, 41.16; Found: C, 44.02; H, 3.01; N, 39.72. Drawing 26:

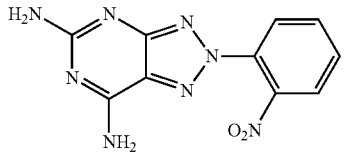

Triethylphosphite was added to the resulting triazole. The mixture was heated to about 140° C. for about 21 hours. The products of this reaction were TAP1 and TAP2. The next step involved nitration by treating TAP1 with about 98% sulfuric acid and about 100% nitric acid and stirring the mixture at about 0°-10° C. for 4 hours. This reaction yielded DNTAP1 and a dinitrobenzotriazole side-product. Similarly, DNTAP2 can be obtained by treating TAP2 with about 98% sulfuric acid and about 100% nitric acid and stirring the mixture at about 0°-10° C. for about 3 hours. This reaction yielded DNTAP2 and a dinitrobenzotriazole side-product.

In one embodiment, the TAP1/TAP2 mixture was nitrated, and DNTAP1/DNTAP2 were isolated in a multistep process. The reaction mixture was poured into ice and extracted with chloroform to remove the dinitrobenzotriazole. Crystals of DNTAP1 were isolated from the refrigerated aqueous layer. The filtrate, which was generated during the isolation of DNTAP1, was neutralized with solid potassium carbonate to a pH of about 8 to 9 to afford DNTAP2 or DNTAP1/DNTAP2.

Actual Methods-Prophetic Results

In another exemplary embodiment, hypofluorous acid (HOF) was reacted with DNTAP1 in an attempt to yield TNMP1. In one example, DNTAP1 was mixed with HOF in aqueous acetonitrile at −15° C. In yet another embodiment, the next step included a nitro Sandmeyer reaction. Sodium nitrite and sulfuric acid in aqueous solution were mixed with DNTAP1, resulting in a yield of uncharacterized product of possibly TNMP1. Alternatively, sodium nitrite and acetic acid were added to DNTAP1 and yielded TNMP1. In an exemplary embodiment, an oxidizer and sulfuric acid were mixed with DNTAP1 to attempt yielding TNMP1. In one exemplary embodiment, the oxidizer included about 30% hydrogen peroxide.

Similarly, TNMP2 may possibly be obtained from DNTAP2. In one exemplary embodiment, the next step included a nitro Sandmeyer reaction. Sodium nitrite and sulfuric acid in aqueous solution were mixed with DNTAP2, resulting in a yield of uncharacterized product of possibly TNMP2. Alternatively, sodium nitrite and acetic acid were added to DNTAP2 to yield TNMP2. In an exemplary embodiment, an oxidizer and sulfuric acid were mixed with DNTAP2 to yield TNMP2. In one exemplary embodiment, the oxidizer included about 30% hydrogen peroxide. In yet another embodiment, hypofluorous acid (HOF) was reacted with DNTAP2 in an attempt to yield TNMP2. In one exemplary example, DNTAP2 was mixed with HOF in aqueous acetonitrile at −15° C.

Actual Methods-Actual Results

In some embodiments, 8.7 mL of triethyl phosphite was added to 0.546 g, 0.00201 mol of the triazole. In some embodiments, the triethyl phosphite was added to a flask containing triazole through a septum on an attached water condenser. The resulting yellow slurry was stirred vigorously at 140° C. for 21 hours and then concentrated in vacuo in a 65° C. water bath giving a yellow precipitate. Crude material was filtered off, washed with hexanes and then triturated vigorously with 9 mL of ethanol for 4 hours to remove excess triethyl phosphite and phosphate by-product. The resulting solid was filtered off, washed with ethanol, and then triturated vigorously with 17 ml of 1/1 acetic acid/ethanol overnight to remove minor organic impurities. The purified material was filtered off, washed with 1/1 acetic acid/ethanol followed by ethanol, and dried under heat and high vacuum to afford 0.268 g (56% isolated yield) TAP1 and TAP2 as a yellow solid. The material was characterized as follows: mp 300° C. (broad dec); NMR (300 MHz, DMSO-$d_6$) δ 8.12-7.23 (m containing 4 pairs total of doublet and triplet peaks along with broad singlet peaks for N—H protons), 1:1.1 ratio of 6.48 (s) and 6.40 (s), respectively; IR: 3328, 3171, 1645, 1608, 1575, 1539, 1505, 1403, 1356, 1213 cm$^{-1}$; MS-DART ionization-positive (m/z): calculated for $C_{10}H_8N_8$ [M+H]$^+$, 241.0950; found, 241.0935. Anal. Calcd. for $C_{10}H_8N_8$: C, 50.00; H, 3.36; N, 46.65; Found: C, 49.16; H, 3.72; N, 45.54.

In addition, crystals of TAP2 suitable for x-ray crystallography were obtained through slow recrystallization of the mixture from approximately 85% aqueous acetic acid. The material was characterized as follows: $^1$H NMR (300 MHz, DMSO-$d_6$) δ 8.02 (d, J=8.4 Hz, 1H), 7.80-7.53 (m, 4H), 7.25 (t, J=8.1 Hz, 1H), 6.48 (s, 2H). Crystals of TAP1 suitable for x-ray crystallography were isolated by slow recrystallization of the mixture from dimethyl sulfoxide and then glacial acetic acid. The material was characterized as follows: $^1$H NMR (300 MHz, DMSO-$d_6$) δ 8.10 (d, J=8.4 Hz, 1H), 7.91 (d, J=8.7 Hz, 1H), 7.62-7.93 (m, 4H), 6.39 (s, 2H)

In some embodiments, 1.3 mL of concentrated sulfuric acid was added to 0.150 g, 0.000625 mol of TAP1 and TAP2 at 3° C. forming a mixture. The resulting slurry was stirred vigorously for 10 minutes. 0.11 mL, 0.00250 mol of white fuming nitric acid was added dropwise, and the resulting mixture was stirred at 0-10° C. for 4 hours. The mixture was pipetted onto ice resulting in an orange/red aqueous solution. The orange/red aqueous solution was extracted with chloroform. The solution was dried over sodium sulfate and concentrated in vacuo to afford 0.023 g of crude dinitrobenzotriazole as an orange solid. The aqueous layer was neutralized to pH 8-9 with approximately 5.0 g of potassium carbonate at 3° C. The resulting orange precipitate was filtered off and washed with ice-chilled water to give a 1.82 g mixture of DNTAP1, DNTAP2 and neutralization salts. The neutralization salts were removed by stirring the mixture vigorously with 18 mL of water for 1.5 hours at room temperature and filtering off insoluble product, affording 0.098 g DNTAP1 and DNTAP2 as an orange solid after drying under mild heat and high vacuum. The material was characterized as follows: DNTAP1/2 (2:1 mixture of isomers): mp 245° C. (broad dec); $^1$H NMR (300 MHz, DMSO-d$_6$) δ 9.45 (m), 9.10 (m). Slow recrystallization from DMSO afforded pure, solvated crystals of DNTAP1 that were suitable for x-ray crystallography. DNTAP1: $^1$H NMR (300 MHz, DMSO-d$_6$) δ 9.43 (d, J=2.1 Hz, 1H), 9.10 (d, J=2.1 Hz, 1H). Further, the aqueous layer could be placed in the refrigerator overnight to give DNTAP1/2 (4:1 mixture of isomers) as a reddish solid. $^1$H NMR (300 MHz, DMSO-d$_6$) δ 9.52 (m), 9.13 (m). Slow recrystallization from DMSO and DMF afforded pure, solvated crystals of DNTAP1 that were suitable for x-ray crystallography. DNTAP1: $^1$H NMR (300 MHz, DMSO-d$_6$) δ 9.52 (d, J=2.1 Hz, 1H), 9.13 (d, J=2.1 Hz, 1H).

It will be understood that many additional changes in details, materials, steps, and arrangements of parts which have been described herein and illustrated in order to explain the nature of the invention, may be made by those skilled in the art within the principle and scope of the invention as expressed in the appended claims Finally, any numerical parameters set forth in the specification and attached claims are approximations (for example, by using the term "about") that may vary depending upon the desired properties sought to be obtained by the present invention. At the very least, and not as an attempt to limit the application of the doctrine of equivalents to the scope of the claims, each numerical parameter should at least be construed in light of the number of significant digits and by applying ordinary rounding.

What is claimed is:

1. A substituted tetraazapentalene compound, of the formula:

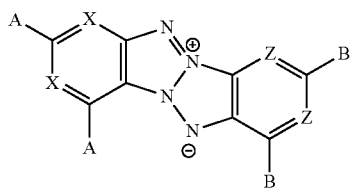

wherein X is nitrogen, wherein A is an amino group, wherein B is one of a nitro group and H, and wherein Z is CH.

2. The substituted tetraazapentalene compound of claim 1, wherein A is an amino group and B is H.

3. The substituted tetraazapentalene compound of claim 1, wherein A is an amino group and B is a nitro group.

4. A substituted tetraazapentalene compound, of the formula:

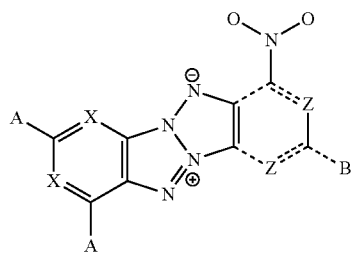

wherein X is N, wherein A is an amino group, wherein B comprises one of a nitro group and H, and wherein Z comprises CH.

5. The substituted tetraazapentalene compound of claim 4, wherein A is an amino group and B is H.

6. The substituted tetraazapentalene compound of claim 4, wherein A is an amino group and B is a nitro group.

7. A triazole compound, of the formula:

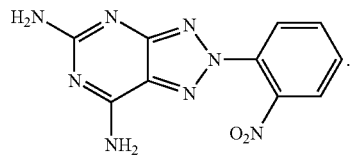

8. A process for producing a 1,2,3-triazole-, comprising:
combining an azo compound of the formula

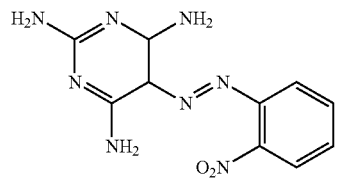

and iodobenzene diacetate in a solvent; and
reacting the azo compound of the formula

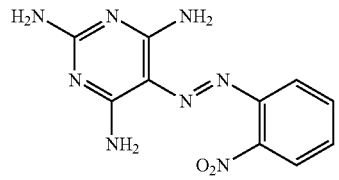

and the iodobenzene diacetate in the solvent for producing a yield of the 1,2,3-triazole-.

* * * * *